(12) United States Patent
Robert et al.

(10) Patent No.: US 11,666,106 B2
(45) Date of Patent: Jun. 6, 2023

(54) LOW FRICTION GLOVE FOR EASY DOUBLE GLOVING

(71) Applicant: O&M Halyard, Inc., Mechanicsville, VA (US)

(72) Inventors: Patrick H. Robert, Alpharetta, GA (US); Shantilal Hirjibhai Modha, Milton, GA (US); Sopha Issara, Songkhala (TH); Ryan S. Solan, Atlanta, GA (US); Mary Rachel Henderson, Decatur, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 1163 days.

(21) Appl. No.: 16/205,421

(22) Filed: Nov. 30, 2018

(65) Prior Publication Data

US 2020/0170320 A1   Jun. 4, 2020

(51) Int. Cl.
| | | |
|---|---|---|
| *A41D 19/00* | (2006.01) | |
| *A41D 19/04* | (2006.01) | |
| *A61B 42/10* | (2016.01) | |
| *A61B 42/50* | (2016.01) | |

(52) U.S. Cl.
CPC ..... *A41D 19/0082* (2013.01); *A41D 19/0075* (2013.01); *A41D 19/043* (2013.01); *A61B 42/10* (2016.02); *A61B 42/50* (2016.02); *A41D 2400/24* (2013.01); *A41D 2400/44* (2013.01); *A41D 2500/52* (2013.01)

(58) Field of Classification Search
None
See application file for complete search history.

(56) References Cited

U.S. PATENT DOCUMENTS

| | | |
|---|---|---|
| 2,425,828 A | 8/1947 | Retzsch et al. |
| 4,102,844 A | 7/1978 | Schwinum et al. |
| 4,851,266 A * | 7/1989 | Momose ............ B29D 99/0067 2/163 |
| 4,888,829 A | 12/1989 | Kleinerman et al. |
| 5,014,362 A | 5/1991 | Tillotson et al. |
| 5,357,636 A | 10/1994 | Dresdner, Jr. et al. |

(Continued)

FOREIGN PATENT DOCUMENTS

| | | |
|---|---|---|
| EP | 1 260 549 A1 | 11/2002 |
| JP | 2014-025160 A | 2/2014 |
| WO | WO 2007/011309 A1 | 1/2007 |

OTHER PUBLICATIONS

Cruse, Phil, "Introduction to the CIE LCH & Lab Colour Spaces", May 17, 2016, 4 pages.

(Continued)

*Primary Examiner* — Ramsey Zacharia
(74) *Attorney, Agent, or Firm* — Dority & Manning, P.A.

(57) ABSTRACT

An elastomeric article includes a first surface and a second surface which is treated with a friction treatment. The elastomeric article can be a glove in which the first surface is an inner donning surface and the second surface is an outer grip surface. The friction treatment reduces friction on the grip surface of the gloves in order to make it easier to don a second glove on top of the grip surface of the gloves of the present invention. The gloves of the present invention may be used as a first pair of gloves in a double-gloving configuration to conform with safety protocols.

19 Claims, 5 Drawing Sheets

(56) References Cited

U.S. PATENT DOCUMENTS

| | | | |
|---|---|---|---|
| 5,486,322 A | 1/1996 | Fuchs | |
| 5,650,225 A | 7/1997 | Dutta et al. | |
| 6,031,042 A * | 2/2000 | Lipinski | C08L 13/02 |
| | | | 524/556 |
| 6,451,893 B1 | 9/2002 | Tao | |
| 6,566,435 B1 | 5/2003 | Teoh et al. | |
| 6,764,731 B2 | 7/2004 | Savoca et al. | |
| 7,176,260 B2 | 2/2007 | Tao | |
| 7,730,554 B2 | 6/2010 | Wang | |
| 7,923,498 B2 | 4/2011 | Foo | |
| 7,971,276 B2 | 7/2011 | Eng et al. | |
| 8,250,672 B2 | 8/2012 | Lipinski et al. | |
| 8,936,843 B2 | 1/2015 | Lipinski et al. | |
| 10,479,874 B1 * | 11/2019 | Amdur | C08K 3/04 |
| 2003/0124354 A1 | 7/2003 | Vistins | |
| 2004/0245670 A1 | 12/2004 | Janssen et al. | |
| 2006/0026737 A1 | 2/2006 | Chen | |
| 2007/0104904 A1 | 5/2007 | Hamann | |
| 2008/0139723 A1 | 6/2008 | Foo | |
| 2008/0311409 A1 | 12/2008 | Lipinski | |
| 2009/0070918 A1 | 3/2009 | Pickard et al. | |
| 2009/0143516 A1 | 6/2009 | MacDonald et al. | |
| 2010/0229282 A1 * | 9/2010 | Eng | A61L 31/10 |
| | | | 2/161.7 |

OTHER PUBLICATIONS

Konica Minolta Sensing Americas, Inc., "Colorimetry—How to Measure Color Differences", Photonics Handbook, Oct. 6, 2015, 3 pages.

Wallemacq, et al., "Permeability of 13 different gloves to 13 cytotoxic agents under controlled dynamic conditions", American Journal of Health-System Pharmacy, vol. 63, Mar. 15, 2006, 9 pages.

* cited by examiner

LOW FRICTION GLOVE FOR EASY DOUBLE GLOVING

FIELD OF THE INVENTION

The present invention relates generally to elastomeric articles that are made from at least one layer of synthetic rubber, and methods of making such articles. In particular, the invention pertains to an elastomeric glove (e.g., surgical, exam, industrial, emergency responder, etc.) with a reduced friction outer surface for easy double gloving, and methods of making such gloves.

BACKGROUND

The development of modern synthetic rubber materials has made possible the manufacture of a wide range of dipped elastomeric articles, such as gloves, balloons, and condoms, having varying properties of strength and chemical resistance. Gloves are used as an infection protection device to protect the wearer from exposure to bacteria, viruses, pathogens, infections, diseases, etc. that could transfer from a surface or bodily fluid (e.g., blood) to the wearer's skin. Gloves are also used in manufacturing environments to prevent the wearer from coming into contact with various chemicals, and in some medical settings, gloves can be used to protect the wearer from certain pharmaceuticals that may be toxic, such as chemotherapy drugs.

New safety protocols in the healthcare environment require double-gloving (i.e. wearing two pairs of examination gloves on top of one another) in an increased number of situations and procedures in order to reduce the risk of exposure to potential contamination or harsh chemicals. The United States Pharmacopeial Convention guidelines USP <800> require double-gloving when handling, administering, compounding, or cleaning up after chemotherapy drugs or any other hazardous drugs. This is because chemotherapy drugs and other hazardous drugs have been shown to be a workplace hazard to those who come into contact with them. Chemotherapy drugs are invisible, long-lasting, easily spread, and capable of causing genetic damage. Moreover, chemotherapy agents have been found on the outside of the drug vials shipped from manufacturers, as well as on floors, counter tops, keyboards, and door knobs. Individuals who handle chemotherapy drugs in their work space have been shown to have chemotherapy drugs present in their urine. However, there is no safe level of exposure to cytotoxic chemotherapy drugs for healthcare workers. Therefore, double-gloving is intended to eliminate or reduce exposure to harmful substances, for example chemotherapy or hazardous drugs, and additionally to reduce cross-contamination of substances.

Nevertheless, despite double-gloving being required, many healthcare practitioners do not implement double-gloving procedures because of the difficulty of donning a second glove on top of the first. Existing medical examination gloves often have an outer grip surface that is tacky and has higher friction than an inner donning surface. The high friction between the outer grip surface of the first glove and the inner donning surface of the second glove prevents them from sliding on top of one another to don the second glove over the first glove. Practitioners who do employ double-gloving practices often do so with much frustration due to the difficulty, the loss of time in sometimes critical situations, and the second gloves sometimes ripping or tearing when trying to don them on top of a first pair.

Whether being used in a medical or manufacturing setting, there is a risk that the gloves could become punctured during use, for example when the gloves are used around sharps such as needles, scissors, blades, hemostats, etc. or equipment used in manufacturing. When such a puncture occurs, the protective barrier provided by the gloves is breached, and the wearer has an increased risk of exposure to bacteria, viruses, pathogens, infections, diseases, harmful substances, etc. It is important that the wearer be made aware of a breach of the protective barrier provided by the gloves, but in most instances, the breach is small (e.g., a puncture, hole, or tear from a small gauge needle), and the wearer may not notice that a breach has occurred. Further, depending on the environment in which the glove is being used, other factors may make the breach difficult to see. For example, the lighting may be poor, or the glove may be soiled or otherwise altered in appearance, making a small puncture nearly impossible to see. Moreover, while two-layered gloves have been available for use, one of the two layers is white, which is accomplished by simply adding titanium dioxide to one of the layers. Because one of the layers is white, breach detection is difficult, particularly in industrial and manufacturing settings, where the wearer of the glove may come in contact with many hazardous materials. Thus, the wearer might not be aware or alerted to the fact that the glove has been breached upon seeing a whitish color present on the glove. Further, the environment surrounding the wearer may include walls, countertops, equipment, lighting, etc. that are white in color or that accentuate a white color, making it difficult for the wearer to discern a visual cue on a white glove.

Consequently, there is a need for gloves having a reduced level of friction on the outer grip side so that the wearer can more easily don a second pair of gloves on top of the first pair to comply with required healthcare industry standards. In particular, a pair of gloves that increases the ease of double-gloving and enables quick identification of punctures, holes, tears, etc. so that the wearer notices immediately that his or her glove has been breached would also be useful.

SUMMARY

The present invention is directed to an elastomeric article, where the article includes a flexible layer of elastomeric nitrile rubber formed from a nitrile rubber emulsion. The article has a first surface and a second surface, and the second surface is treated with a friction treatment that reduces the level of friction of the second surface to improve the ease with which a second elastomeric article can slide on top of the second surface.

In one particular embodiment, the article is a glove.

In addition, the first surface can be a donning side of the glove and the second surface can be a grip side of the glove.

In another embodiment, the first surface and the second surface can be chlorinated.

Further, the chlorination of the first surface and the chlorination of the second surface can be accomplished with different chlorine solutions.

Moreover, the first surface can be chlorinated with hypochlorous acid and the second surface can be chlorinated with a solution of chlorine gas in water.

Additionally, the nitrile rubber emulsion can include a solids content of between about 15 percent and about 30 percent, by weight.

In yet another embodiment, the nitrile rubber emulsion includes a defoamer.

In still another embodiment, coagulation of the nitrile rubber emulsion to form the elastomeric article can be accelerated by a metallic salt, wherein the metallic salt includes nitrate, sulfate, or chloride salts of calcium, aluminum, or zinc, or a combination thereof.

In addition, the friction treated second surface can have less friction compared to an identically formed elastomeric article that has not been treated with the friction treatment.

In one particular embodiment, the second surface can have a static coefficient of friction in a range from about 0.3 to about 0.9.

In still another embodiment, the second surface can have a dynamic coefficient of friction in a range from about 0.3 to about 1.

The present invention additionally relates to a process for making an elastomeric article, the process including steps of: coating a surface of a former with a coagulant solution; immersing the former into a nitrile rubber emulsion to form a layer of coagulated nitrile rubber on the former surface, the coagulated nitrile rubber forming an elastomeric article on the former, the elastomeric article having a first surface that is exposed from the former and a second surface contacting the former; chlorinating the first surface of the elastomeric article; curing the elastomeric article; removing the elastomeric article from the former and inverting the elastomeric article such that the chlorinated first surface of the elastomeric article becomes an interior surface of the elastomeric article; and subjecting the inverted elastomeric article to a friction treatment to reduce the friction of the exterior-facing second surface of the elastomeric article.

Additionally, elastomeric article can be a glove, further wherein the first surface can form a donning surface of the glove and the second surface can form a grip surface of the glove.

Moreover, the nitrile rubber emulsion can include a solids content of between about 15 percent and about 30 percent, by weight.

In addition, the nitrile rubber emulsion can be pigmented such that the elastomeric article is colored by the pigment.

Further, the step of immersing the former into the nitrile rubber emulsion can last for a dwell time sufficient to form a layer of coagulated nitrile rubber on the former surface having a thickness in the range of about 0.06 mm to about 0.14 mm.

Moreover, the step of chlorinating the first surface of the elastomeric article can include dipping the former containing the elastomeric article into a first solution comprising from about 1.5 wt % to about 4.5 wt % sodium hypochlorite, then transferring the former containing the elastomeric article to a tank containing a second solution comprising from about 0.1 wt % to about 1.5 wt % hydrochloric acid.

In addition, the former containing the elastomeric article can be dipped into a series of water tanks at about 85° C. to about 95° C. after the step of transferring the former containing the elastomeric article to the tank containing the second solution.

Further, the friction treatment can include immersing the inverted elastomeric article into a chlorinating bath to chlorinate the exterior-facing former surface of the elastomeric article.

Additionally, the step of immersing the inverted elastomeric article into the chlorinating bath can include transferring the inverted elastomeric article to a tank containing a chlorine solution containing about 600 ppm to about 2200 ppm of chlorine gas dissolved in water and tumbling the elastomeric article in the solution within the tank.

Moreover, the process can further include a step of draining the chlorine solution to waste and filling the tank with water to clean the chlorinated elastomeric article of any residual chlorine left on the second surface of the elastomeric article.

The present invention additionally relates to a kit for double-gloving. The kit can include a first elastomeric glove formed from a flexible layer of elastomeric nitrile rubber formed from a nitrile rubber emulsion, the glove having a chlorinated first surface and a friction treated second surface; and a second elastomeric glove for donning on top of the first elastomeric glove. The friction treatment of the second surface of the first elastomeric glove can reduce the level of friction of the second surface to improve the ease with which the second elastomeric glove can slide on top of the second surface to don the second elastomeric glove on top of the first elastomeric glove.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

A desirable attribute for elastomeric articles that are worn on the body is softness or pliability of the polymeric material. The present invention describes the creation of elastic articles, such as gloves, made from a nitrile polymer formulation. As used herein, the terms "elastic" or "elastomeric" generally refer to a material that, upon application of a force, is stretchable to an extended, biased length. Upon release of the stretching, biasing force, the material will substantially recover to near net shape or original dimensions.

Generally speaking, the present invention is directed to the creation of elastomeric articles, for example gloves, having a flexible layer of an elastomeric nitrile rubber formed from a nitrile rubber emulsion, each glove having a first, donning surface and a second, grip surface, wherein the grip surface is treated with a friction treatment that reduces the level of friction of the grip surface to improve the ease with which a second elastomeric article, e.g. a second glove, can slide on top of the grip surface. The specific features of the elastomeric glove of the present invention may be better understood with reference to FIGS. 1-4.

Figure 1:
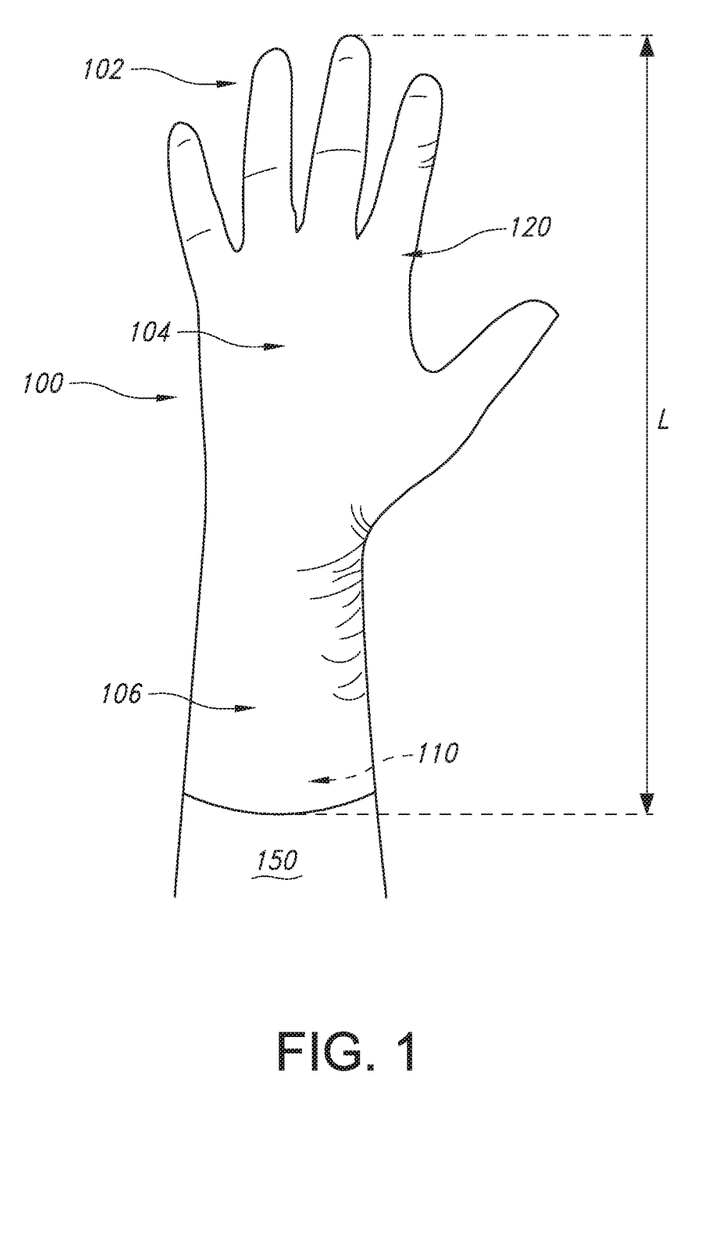
FIG. 1 illustrates a perspective view of the elastomeric glove of the present invention.

Referring now to FIG. 1, the elastomeric glove 100 is made from an elastomeric substrate and includes a finger region 102, a palm region 104, and a forearm or cuff region 106. The glove 100 has an inner donning surface 110 and an outer grip surface 120. The inner donning surface 110 is configured to contact the wearer's skin and is made to be smooth and silky to reduce friction when donning the glove 100 on the wearer's hand. The outer grip surface 120 of the glove 100 of the present invention is configured to be exposed away from the wearer and typically has an enhanced gripping texture compared to the donning surface 110. However, the grip surface 120 is made sufficiently smooth through a friction treatment (described in detail below) to reduce friction when donning a second glove (see, e.g., FIGS. 2-3) over the glove 100. The cuff region 106 of the glove 100 may extend beyond the wearer's wrist and over a portion of the wearer's forearm 150. The glove 100 may have a total average length L from the finger region to the cuff region of about 200 mm to about 400 mm (about 8 to about 16 inches), such as from about 250 mm to about 355 mm (about 10 to about 14 inches), for example about 310 mm (about 12 inches). The extended length of the glove may provide additional coverage to a wearer. For example a healthcare professional handling chemotherapy drugs may employ the extended length of the cuff 106 of the glove 100 under a cuff of a chemotherapy gown for additional coverage.

Figure 2:
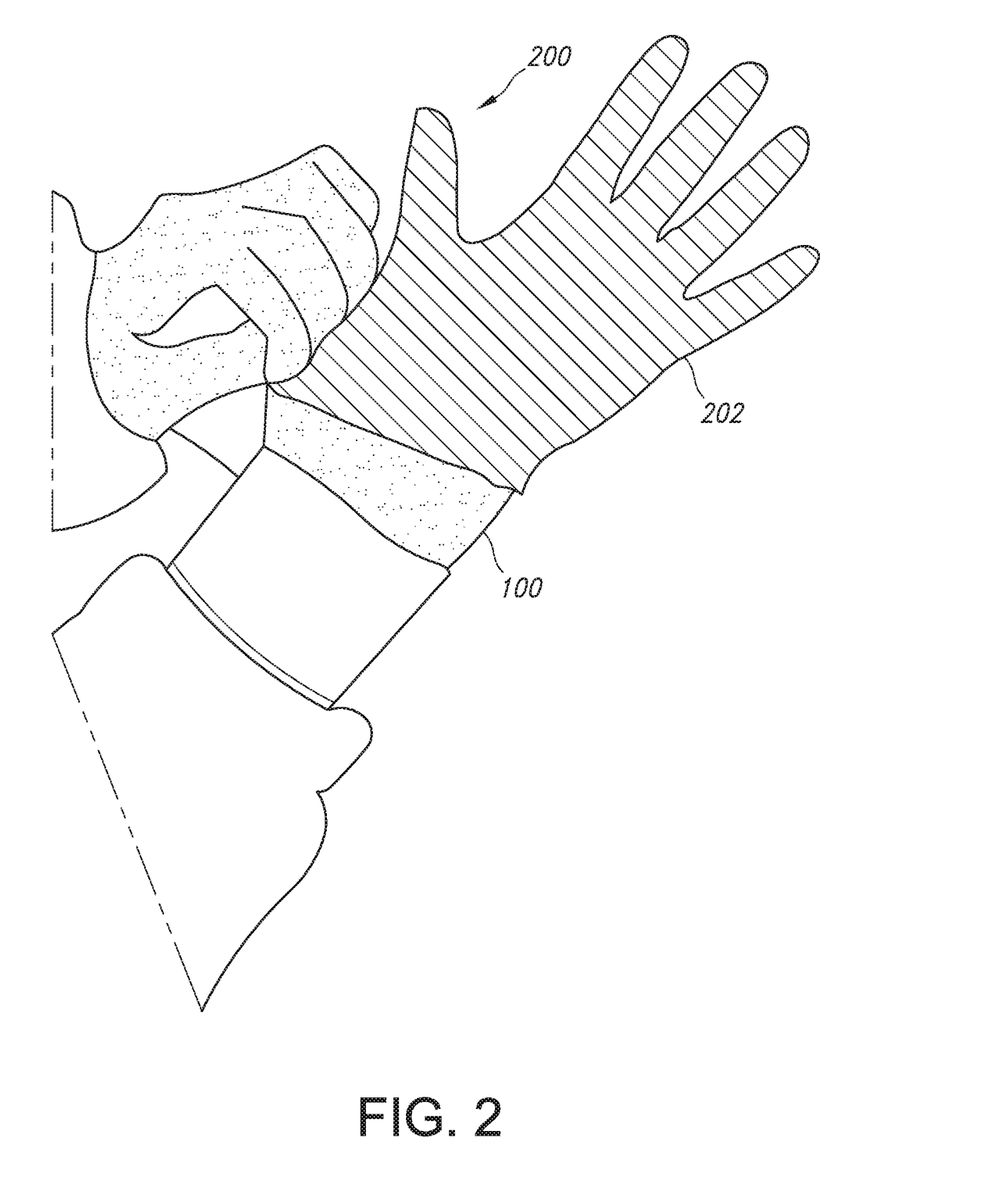
FIG. 2 illustrates a perspective view of a double-gloving assembly including the elastomeric glove of FIG. 1 and a second elastomeric glove.
Figure 3:
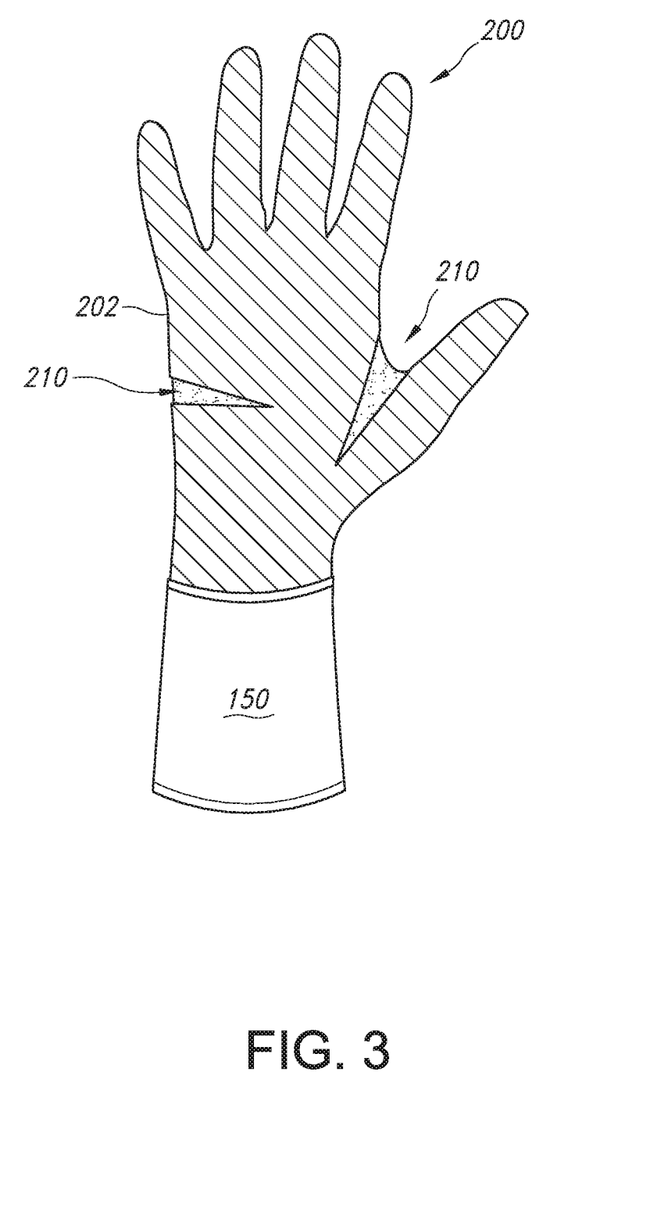
FIG. 3 illustrates a perspective view of a double-gloving assembly, including the elastomeric glove of FIG. 1 and a second elastomeric glove, having breach detection features.

A double-gloving configuration is shown in FIGS. 2 and 3. In an exemplary double-gloving assembly 200, the elastomeric glove 100 of the present invention is donned as a first or inner glove, and a second or outer glove 202 is donned on top of the glove 100. The first inner glove 100 may be termed an "underguard" glove because it provides an inner barrier in the double-gloving configuration. The first or inner elastomeric glove 100 may have a distinct color. For example, inner glove 100 may be pink pigmented. The second or outer glove 200 may be another glove 100 of the present invention (not shown) or it may be a different glove 202, as shown in FIGS. 2 and 3. For example, the second or outer glove 202 may be a different brand, thickness, length, color, etc. FIGS. 2 and 3 illustrate a second glove 202 having a different color or appearance than inner glove 100, which is depicted by the different patterns shown in the Legend of FIG. 2. As illustrated in FIG. 3, when a second glove 202 having a different color is worn over the glove 100, a breach 210 of the outer surface of the second glove 202 can be easily detected since the grip surface 110 of the glove 100 can be visible through the breach (e.g., puncture or tear) of the outer glove 202. In the double-glove assembly 200 of FIGS. 2 and 3, the second glove 202 and the first inner glove 100 of the double-glove assembly 200 have the same dimensions. However, in other embodiments, a second glove 202 may have different dimensions (e.g., a shorter cuff region 106) than the first inner glove 100.

Using the protocol described in ASTM D3767, procedure A, glove thicknesses are measured by taking an elastomeric substrate portion from an exemplary glove 100. The elastomeric substrate can have an average thickness ranging from about 0.03 mm to about 0.18 mm, for example from about 0.05 mm to about 0.15 mm. When made into a glove 100, according to certain embodiments, the substrate can have a thickness in the palm region of about 0.06 mm to about 0.14 mm. More desirably, the substrate can have a thickness in the palm region ranging from about 0.09 mm to about 0.11 mm, for example about 0.10 mm. The glove 100 may have a thickness in the middle finger region ranging from about 0.08 mm to about 0.16 mm, for example about 0.12 mm. The glove 110 may have a thickness in the cuff region 106 ranging from about 0.04 mm to about 0.10 mm, for example about 0.07 mm.

The gloves made using the current invention are less bulky and more pliable to wear, providing greater comfort compared to conventional nitrile rubber gloves. With a thinner material (e.g. desired palm thickness of about 0.09-0.10 mm and desired middle finger thickness of about 0.12 mm), the wearer also enjoys greater tactile sensation in the hand and finger tips than compared with regular gloves.

Furthermore, after aging at 70° C.+/−2° C. for 168 hours+/−2 hours, a glove 100 made according to the present invention with a thickness of 0.09-0.10 mm in the palm area may have a tensile strength ranging from about 35 MPa to about 40 MPa, for example about 38 MPa. Further, the aged glove can have an ultimate elongation at break ranging from about 450% to about 650%, such as from about 500% to about 600%, for example about 550%.

The precise point of measurement in order to determine that data described above is that defined in American Society for Testing and Materials (ASTM) test standard D-412-98a (Reapproved 2002), "Standard Test Methods for Vulcanized Rubber and Thermoplastic Elastomers—Tension, published January 2003, the contents of which are incorporated herein by reference. These test methods cover procedures used to evaluate the tensile (tension) properties of vulcanized thermoset rubbers and thermoplastic elastomers. The determination of tensile properties starts with test pieces taken from a sample material and includes the preparation of specimens and the testing of the specimens. Specimens may be in the shape of dumbbells, rings, or straight pieces of uniform cross-sectional area. Measurements of tensile stress, tensile stress at a given elongation, tensile strength, yield point, and ultimate elongation are made on specimens that have not been pre-stressed. Tensile stress, tensile strength, and yield point are based on the original cross-sectional area of a uniform cross-section of the specimen.

The elastomeric article or glove of the present invention may further have a static coefficient of friction in a range from about 0.3 to about 0.9, such as from about 0.4 to about 0.8, for example from about 0.5 to about 0.7. The elastomeric article or glove of the present invention may further have a dynamic coefficient of friction in a range from about 0.3 to about 1.0, such as from about 0.4 to about 0.9, for example from about 0.55 to about 0.75.

Various glove layer components, glove formation procedures, and several examples contemplated by the present invention are discussed in more detail below.

Nitrile Rubber Formulation

The elastomeric article or glove of the present invention may generally be formed from any of a variety of natural and/or synthetic elastomeric materials known in the art. For instance, some examples of suitable elastomeric materials include, but are not limited to, nitrile rubbers (e.g., acrylonitrile butadiene), polyurethanes, S-EB-S (styrene-ethylene-butylene-styrene) block copolymers, S-I-S (styrene-isoprene-styrene) block copolymers, S-B-S (styrene-butadiene-styrene) block copolymers, S-I (styrene-isoprene) block copolymers, S-B (styrene-butadiene) block copolymers, natural rubber latex, isoprene rubbers, chloroprene rubbers, neoprene rubbers, polyvinyl chlorides, silicone rubbers, and various combinations thereof. In an exemplary embodiment, the glove is made from nitrile rubber.

Nitrile-butadiene rubber (commonly referred to as "nitrile rubber" or "NBR") is a family of amorphous unsaturated copolymers of acrylonitrile and various butadiene monomers (1,2-butadiene and 1,3-butadiene). This form of synthetic rubber is generally resistant to aliphatic hydrocarbons, such as fatty tissue, oils, and other chemicals. Nitrile rubber has been used to create molded goods, footwear, adhesives, sealants, sponge, expanded foams, and floor mats. Its resilience makes conventional nitrile rubber a good material for disposable gloves used in laboratory, cleaning, industrial work, and clinical situations. Conventional medical exam gloves made from conventional nitrile rubber generally are three times more puncture-resistant than conventional medical exam gloves made from natural rubber (i.e., formed from natural rubber latex) or polyvinyl chloride.

As a disposable product, a nitrile rubber glove made according to the present invention will have a mass that is at least about 40-50% less than a typical polyvinyl chloride-based glove of the same type (e.g., medical exam, household, or industrial) and size (i.e., small, medium, large, x-large). For example, a nitrile rubber medical exam glove according to the present invention that is made to the conventional size "M" or "Medium" will have a mass that is at least about 40 percent to about 50 percent less (or an even greater percentage less) than a typical polyvinyl chloride medical exam glove that is made to the conventional size "M" or "Medium".

As previously noted, various published reports describing comparative testing of conventional polyvinyl chloride medical exam gloves and nitrile rubber medical exam gloves show that polyvinyl chloride medical exam gloves have a greater incidence of leakage. Given that vinyl is inherently a much weaker material in terms of tensile strength and is likely to have pinholes in the membrane, vinyl-based medical exam gloves require the use of a greater amount of material to achieve the same level of strength and integrity as a nitrile rubber medical exam glove of the present invention. Thus, the nitrile rubber medical exam gloves of the present invention contribute relatively less waste and have less environmental impact because they have substantially less mass than comparable polyvinyl chloride medical exam gloves.

From a commercial viewpoint, the nitrile rubber medical exam gloves of the present invention are cost competitive with inexpensive polyvinyl chloride medical exam gloves. That is, the thinner nitrile rubber gloves of the present invention are more affordable than conventional nitrile rubber gloves that are thicker products. The relatively lower cost of the thinner nitrile rubber gloves of the present invention provides more opportunities for consumers to switch from polyvinyl chloride gloves to a better performing nitrile rubber glove (e.g., fewer pinhole defects and better stretch/tensile properties) without much adverse economic impact in addition to avoiding exposure to hazardous components such as diethylhexylopthalate (DEHP) which can leach from polyvinyl chloride gloves.

The nitrile rubber that can be used to form one of the layers can include a carboxylated nitrile that is compounded with various components based on 100 parts of the carboxylated nitrile. The carboxylated nitrile rubber and the various components compounded with the nitrile rubber in the formulation of the present invention are discussed in more detail below.

Carboxylated nitrile, which is a terpolymer of butadiene, acrylonitrile, and organic acid monomers, has at least two properties that make it useful for manufacturing elastomeric articles. These two features are high strength and impermeability to certain hydrocarbon solvents and oils. Compounding and curing the rubber with other ingredients such as curing agents, accelerators, and activators is generally performed to optimize these properties. The level of each monomer in the polymer and the level of curing can affect the levels of strength and the chemical resistance in the finished article. Polymers with higher levels of acrylonitrile tend to have better resistance to aliphatic oils and solvents, but are also stiffer than polymers that have lower levels of acrylonitrile. While the chemical nature of the monomers from which the polymer is made offers some degree of chemical resistance, when the polymer molecules are chemically crosslinked, resistance to chemical swelling, permeation, and dissolution greatly increase.

The base polymer employed in the nitrile rubber can be a random terpolymer composition containing acrylonitrile, butadiene, and carboxylic acid components. It is believed that the particular advantageous properties of the present soft nitrile rubber materials can be due in part to the nature and interaction of a blend of acrylonitrile components in the composition. The blend can include two—a first and a second—acrylonitrile formulations in a compositional ratio ranging, respectively, from about 60:40 to 40:60. The orientation or placement of carboxyl groups on the nitrile polymer molecules—either outside or inside—can affect the reactivity of the carboxyl groups with zinc ions; hence, it is believed that some components exhibit softer, lower modulus properties and some components have good film forming properties.

The acrylonitrile content of the blended or combined terpolymer composition can range from about 17% by weight to about 45% by weight, such as from about 20% by weight to about 40% by weight, such as from about 20% by weight to about 35% by weight. In one embodiment, for instance, the acrylonitrile content can be between about 22% by weight and about 28% by weight, the methacrylic acid content can be less than about 10% by weight, and the remainder of the polymer can be butadiene. The methacrylic acid content should be less than about 15% by weight, preferably about 10% by weight, with butadiene making up the remainder balance of the polymer. The base terpolymer is made through a process of emulsion polymerization, and can be used while still in emulsion form to manufacture gloves or other elastomeric articles.

Further, the acrylonitrile polymer formulations that may be employed in the present invention can have a glass transition temperature (Tg) ranging from about −30° C. to about −10° C., such as from about −28° C. to about −12° C. In some embodiments, desirable nitrile polymer formulations, such as PolymerLatex X-1133 or Synthomer 6311 available from PolymerLatex GmbH, and Synthomer Ltd., respectively, can have a Tg between about −26° C. and about −18° C. Other nitrile formulations, such as Nantex® 635t, commercially available from Nantex Industry Co., Ltd. (Taiwan, R.O.C.), can have a Tg between about −25.5° C. and about −23.4° C. Another suitable nitrile polymer contemplated for use in the elastomeric articles of the present invention is Lutex 111 manufactured by LG Chem, which has a Tg ranging from about −22° C. to about −14° C. and a total solids content of about 44.5% to about 45.5% and a pH of from about 8.2 to about 8.8.

It is believed, however, that the nitrile butadiene polymer properties do not come from components of the nitrile material, but from the structure of the polymer, which in turn, is determined by polymerization conditions. Polymer properties are very much affected by the polymer structure. Molecular structure of polymers can be very complex, with variability in molecular weight, molecular weight distribution, amount of branching, amount of crosslinking during polymerization, many possible types of chemical addition for diene monomers, etc. When several monomer types are combined into a polymer such as in a carboxylated acrylonitrile butadiene polymer used for glove manufacture, the structure becomes even more complex. Overall levels of each monomer type and the sequencing of the monomer units also contribute to the properties of the resulting polymer. When the repeating structure of the monomer units is random, such as in the nitrile rubber used for gloves, the physical properties of the polymer have increased influence from the polymer linearity (vs. branching) and molecular weight as compared to the properties of a homopolymer. This is because the properties expected from a regular repeating structure of a polymer made only from each single monomer change once that repeating structure is interrupted or otherwise altered by the addition of other types of monomer units. A high level of any particular monomer will likely increase the chance of contributing properties expected from a homopolymer made from that monomer, due to increased similarity of the repeating structures.

In carboxylated nitrile rubber used for thin glove manufacture, the acrylonitrile and carboxylic acid, which typically total approximately 35% by weight, add some plastic like character to the polymer with respect to resilience, permanent set, and stress relaxation. They also prevent a regular cis-1,4 repeating structure that would give polybutadiene its highest resilience and lowest set/relaxation.

A general description of such a carboxylated nitrile rubber would be a long-chain random arrangement of its three component monomers, with branching and crosslinking. These branched, random terpolymers are former into discrete tiny particles that are emulsified in water. In addition to the polymer structure, the particle structure also plays a part in the final properties of a glove. Parameters such as particle size, particle size distribution, level of particle agglomeration, particle density, etc., affect how the product is formed, and also its eventual properties.

Although not required, the polymer structure can include a random terpolymer (as opposed to block or alternating terpolymer) of acrylonitrile, butadiene, and carboxylic acid. The properties depend on the average molecular weight, the molecular weight distribution, the linearity or degree of branching, the gel content (crosslinking during polymerization), and the microstructure (which monomer units are next to each other in short sections of the polymer chain).

Regardless of the particular structure of the nitrile rubber that can be used in one or more layers of the glove of the present invention, various additional components, such as but not limited to an alkali agent, a metal oxide, sulfur, pigment, an accelerator, a defoamer, and a surfactant, can be incorporated during the compounding of the nitrile rubber formulation so that the overall glove can have certain desired properties.

For instance, an alkali agent can be added to the nitrile rubber formulation to adjust the pH of the nitrile rubber formulation. Any suitable alkali agent can be used, and, in some embodiments, the alkali agent can be potassium hydroxide, ammonium hydroxide, or a combination thereof. In any event, the alkali agent can be used to adjust the nitrile rubber formulation to a pH that can range from about 9 to about 11, such as from about 9.2 to about 10.5, such as from about 9.5 to about 10.2. In addition to acting as a pH adjuster, the alkali agent can be utilized in combination with a metal oxide as discussed below to facilitate the formation of a nitrile rubber formulation that has high strength. Specifically, the alkali agent can include monovalent ions, such as K, Na, or H, which, although they do not have sufficient electron capacity to accommodate a bond with a second methylacrylic acid unit, may allow for weaker forms of associative bonding. As such, the alkali agents (e.g., monovalent salts) that can be used to increase the pH of the nitrile rubber formulation may also swell the nitrile rubber particles, making more carboxylic acid groups accessible to other crosslinking agents, such as the metal oxides discussed in more detail below. The positive charge of the cation can well balance the negative electrons of the acidic carboxyl groups.

Regardless of the particular alkali agent utilized, the alkali agent can be present in the compounded nitrile rubber formulation in an amount ranging from about 0.1 parts to about 2 parts, such as from about 0.25 parts to about 1.8 parts, such as from about 0.5 parts to about 1.6 parts, based on 100 dry parts of the nitrile rubber.

Further, the nitrile rubber formulation that can be used in one or more layers of the elastomeric glove of the present invention can be chemically crosslinked to enhance the elasticity, strength, and chemical resistance of the nitrile rubber formulation. Crosslinking can be accomplished in at least two ways: the butadiene subunits can be covalently crosslinked with sulfur and accelerators, while the carboxylated (organic acid) sites can be ionically crosslinked with metal oxides or salts. Ionic crosslinks, resulting from, for example, the addition of a metal oxide, such as zinc oxide, to the nitrile rubber formulation, can result in a nitrile rubber formulation having high tensile strength, puncture resistance, and abrasion resistance, as well as high elastic modulus (a measure of the force required to stretch a film of the rubber), but poor oil and chemical resistance, which is why a sulfur crosslinking agent can be added to the nitrile rubber formulation, as discussed in more detail below.

Including a metal oxide, such as zinc oxide, in the nitrile rubber formulation can improve the dipping qualities and cure rates of the formulation. In contrast, when zinc oxide is not employed, the curing time required to reach an optimum state of cure can be much longer and the curing may be less efficient. This means that the crosslinks are longer (more sulfur atoms per crosslink) and there may be a higher amount of sulfur that does not crosslink polymer chains. The result can be a less-effectively cured rubber that has lowered heat resistance and less chemical resistance.

While not intending to be bound by theory, it is believed that the matrix structure and strength of the nitrile rubber formulation that can be used in one or more layers of the glove of the present invention may result from the interaction of all ions present in the system, in particular, divalent or higher valence cations, with the carboxylic acid components of the polymer matrix. Divalent or multivalent cations, such as Mg, Ca, Zn, Cu, Ti, Cd, Al, Fe, Co, Cr, Mn, and Pb, can crosslink with the carboxyl groups of the ionized carboxylic acids, forming relatively stable bonds. Of these cation species, Mg, Ca, Zn, Cu, or Cd are more desirable. Preferably, the methylacrylic acid monomers are located relatively close to each other in the polymer matrix structure; in such a fashion, the divalent or multivalent cation can crosslink with two or more nearby acid units. The positive charge of the cation can well balance the negative electrons of the acidic carboxyl groups. It is believed that, absent divalent or multivalent cations, multiple polymer chains in the nitrile emulsions are not well crosslinked together.

Regardless of the particular metal oxide utilized, the metal oxide can be present in the compounded nitrile rubber formulation in an amount ranging from about 0.1 parts to about 2 parts, such as from about 0.25 parts to about 1.75 parts, such as from about 0.3 parts to about 1.5 parts, based on 100 dry parts of the nitrile rubber.

As mentioned above, a sulfur crosslinking agent can also be used in the nitrile rubber formulation to provide oil and chemical resistance to a layer of a glove containing the formulation. Such crosslinking can provide resistance to chemical swelling, permeation, and dissolution. In contrast to the alkali agent and metal oxide crosslinking agents discussed above, the sulfur is used to covalently crosslink the butadiene subunits of the carboxylated nitrile rubber. Sulfur can be present in the compounded nitrile rubber formulation in an amount ranging from about 0.1 parts to about 5 parts, such as from about 0.2 parts to about 2.5 parts, such as from about 0.5 parts to about 2 parts, based on 100 dry parts of the nitrile rubber.

A vulcanization accelerator can be used in combination with the sulfur crosslinking agent to provide the desired level of chemical resistance to the nitrile rubber formulation. As with the sulfur crosslinking agent, the vulcanization accelerator can be used to covalently crosslink the butadiene subunits of the carboxylated nitrile rubber. The vulcanization accelerator can be a single dithiocarbamate accelerator that is added with sulfur. However, in other cases where higher levels of chemical resistance are needed, a combination of vulcanization accelerators can be utilized. For example, the vulcanization accelerator can be zincediethyldithiocarbamate (ZDEC), zinc mercaptobenzothiazole (ZMBT), diphenyl guanidine (DPG), or a combination thereof.

Regardless of the particular vulcanization accelerator or combination of vulcanization accelerators utilized, the vulcanization accelerator can be present in the compounded nitrile rubber formulation in an amount ranging from about 0.1 parts to about 5 parts, such as from about 0.2 parts to about 2.5 parts, such as from about 0.4 parts to about 2 parts, based on 100 dry parts of the nitrile rubber.

Moreover, the nitrile rubber formulation of the present invention can include one or more of a titanium dioxide or similar filler, a color pigment, or a combination thereof to provide a desired level of color, contrast, brightness, saturation, value, and/or opaqueness. Specifically, the compounded nitrile rubber formulation can include titanium dioxide or any other similar filler in an amount ranging from about 0.25 parts to about 5 parts, such as from about 0.5 parts to 4.5 parts, such as from about 1 parts to about 4 parts, based on 100 dry parts of the nitrile rubber. Without intending to be limited by any particular theory, the present inventors have found that the inclusion of titanium dioxide or any other similar filler in such amounts can prevent the bleed through of a color pigments between various layers of the glove in a multi-layer glove. Further, the compounded nitrile rubber formulation can include a lighter colored pigment (e.g., red, orange, yellow, green, blue, indigo, violet, or a combination thereof) or a darker colored pigment (e.g., black, brown, dark gray, blue, purple, etc.) in an amount ranging from about 0.25 parts to about 2 parts, such as from about 0.5 parts to about 1.5 parts, such as from about 0.75 parts to 1 part, based on 100 dry parts of the nitrile rubber. One example of a violet pigment may be a quinacridone. Moreover, the present inventors have discovered that the ratio of the parts of titanium dioxide to the colored pigment in the nitrile rubber formulation can be controlled to achieve a glove layer having desired saturation (color purity) and value (lightness or darkness) percentages. Specifically, the ratio of parts of titanium dioxide to the parts of colored pigment in the nitrile rubber formulation can range from about 0.25 parts to about 20 parts titanium dioxide per parts of colored pigment, such as from about 0.5 parts to about 10 parts titanium dioxide per part of colored pigment, such as from about 1 part to about 5 parts titanium dioxide per part of colored pigment.

Further, the nitrile rubber formulation may include a defoamer. The defoamer can prevent and/or break bubbles in the nitrile rubber formulation emulsion. As a result, the use of a defoamer in the nitrile rubber formulation can give substantial freedom from defects such as fisheyes and surface imperfections during formation of the nitrile rubber film on the mold or former. In some embodiments, the defoamer may be an emulsifiable, Silica-type, oil based defoamer and an anti-webbing agent. In some embodiments, the defoamer may be present in an amount ranging from about 0.005 to about 1 part based on 100 dry parts of the nitrile rubber, such as from about 0.01 to about 0.75 parts based on 100 dry parts of the nitrile rubber, such as from about 0.015 to about 0.5 parts based on 100 dry parts of the nitrile rubber.

Regardless of the specific components utilized to form the nitrile rubber formulation of the present invention, after compounding, the resulting nitrile rubber formulation can have an as-received total solids content (TSC) of about 40-45%. The nitrile rubber solids content of the emulsion can be diluted to form a bath of nitrile rubber emulsion that is suitable for forming the glove to be coated on the former to create a bath having nitrile rubber solids content to form a glove of the desired thickness. The nitrile rubber solids content of the bath can have a TSC ranging from about 15% to about 30%, such as from about 17.5% to about 27.5%, such as from about 20% to about 25%. The reduction of the TSC by dilution enables for the manufacture of single- or multi-layered elastomeric articles that have a reduced thickness compared to some other elastomeric articles. Further, it is to be understood that the components of the nitrile rubber formulation can be compounded by adding them to the nitrile rubber formulation in any order.

After the nitrile rubber formulation is compounded, the formulation can be used to form various layers of any suitable elastomeric article. In one particular embodiment, the nitrile rubber formulation can be used to form a glove having reduced friction on an outer surface for easier double-gloving, as discussed in more detail below.

Coagulant Solution

After the nitrile rubber formulation is compounded, the formulation can be used in a coagulant dip-coating process to form an elastomeric article such as an elastomeric glove. In this process, a mold or "former" is dipped into an aqueous coagulant solution prior to dipping the former into the nitrile rubber formulation to cause gelation of the nitrile rubber over the mold or former surface. The coagulant solution comprises a powder free coagulant that includes one or more metallic salts as a coagulating agent (e.g., nitrate, sulfate, or chloride salts of calcium, aluminum, or zinc, or a combination thereof). In one embodiment, the coagulating agent may be calcium nitrate. The metallic salts can be present in the solution in an amount ranging from about 5 wt % to about 20 wt %, such as from about 7.5 wt % to about 17.5 wt %, such as from about 10 wt % to about 15 wt % based on the total weight of the solution. The metallic salt, e.g. calcium nitrate, in the coagulant formulation is the source for ions that trigger subsequent coagulation.

In addition to a powder free coagulant, the solution can include one or more other components. For instance, the solution can include a wax, a release agent, a hydrogel, a silicone, a gel, an antimicrobial agent (e.g., silver (Ag++), copper (Cu++), polyhexamethylene biguanide (PHMB), etc.), an acrylic polymer, a peroxide crosslinking agent, an emollient (e.g., shea butter, petroleum, etc.), a hydrophilic agent, a hydrophobic agent, a colorant, a dye, a polyolefin-based powder (e.g., a polyethylene powder or a polypropylene powder), a surfactant, a soap, an acidic agent, an alkali agent, a defoamer, or a combination thereof. These additional components can be present in the solution in a cumulative amount ranging from about 0.1 wt % to about 30 wt %, such as from about 0.5 wt % to about 25 wt %, such as from about 1 wt % to about 20 wt % based on the total weight of the solution.

A surfactant can be included in the coagulant solution to provide enhanced wetting to and of the former. The enhanced wetting of the former is particularly useful with respect to an elastomeric article made by multiple dips of the former into the nitrile rubber emulsion.

A defoamer can be included in the coagulant solution to prevent bubbles in the coagulant solution. The defoamer may be an oil-based defoamer and anti-webbing agent that promotes wetting of other low energy substrates, such as plastics and contaminated or improperly cleaned surfaces. The defoamer may be present in the coagulant solution in an amount ranging from about 0.001 wt % to about 1 wt %, such as from about 0.002 wt % to about 0.75 wt %, such as from about 0.003 wt % to about 0.5 wt %.

According to the present invention, the coagulant solution can include a release agent. The release agent is in the form of a "waxy" material and is used in the fabrication of a powder-free dipped article. The release agent can be an anti-tack agent that is a rubber lubricant mixed into the coagulant solution to aid in preventing the coagulated nitrile rubber article from sticking to the mold or former. The release agent is typically a low-melting organic mixture or compound of high molecular weight, solid at room temperature and generally similar to fats and oils except that it contains no glycerides. For example, the release agent can be: an inorganic powder (e.g., carbonates, stearates, oxides, hydroxides, aluminates, etc.); a petroleum wax with a melting point of less than about 200° C. (e.g., melting point between about 135° C. to about 180° C.) which can be in the form of paraffin waxes, microcrystalline waxes, or petroleum jelly; a natural animal or insect wax such as bee's wax; or a synthetic wax (e.g., polyethylene waxes). Generally speaking, the release agent can be emulsified in the coagulant solution and can be present in an amount ranging from about 0.1 wt % to about 10 wt %, such as from about 0.5 wt % to about 7.5 wt %, such as from about 1 wt % to about 5 wt %, such as about 2.5 wt %. The release agent can aid in the subsequent release of the completed elastomeric article from the former with minimal to no loose particulates.

A combination of release agents may be used in the coagulant solution. For example, the release agent may be a salt or ester of stearic acid, for example having the formula $Ca(O_2C_{18}H_{35})_2$ or calcium stearate. Calcium stearate may be in the form of a water-based polymer lubricant dispersion such as Nobel 7001. Another example of a release agent is an inorganic powder, for example calcium carbonate. In one particular embodiment, both calcium stearate and calcium carbonate may be used as release agents in the coagulant solution. The ratio of calcium carbonate to calcium stearate present in the coagulant solution may range from about 1:5 to about 1:15, such as from about 1:7.5 to about 1:12.5, for example about 1:10. The calcium carbonate may be present in an amount ranging from 0.05 wt % to about 5 wt %, such as from about 0.1 wt % to about 2.5 wt %, such as about 0.15 wt % to about 1 wt %. The calcium stearate may be present in an amount ranging from about 0.1 wt % to about 10 wt %, such as from about 0.5 wt % to about 7.5 wt %, such as from about 1 wt % to about 5 wt %, such as about 2 wt %.

A remainder of the coagulant solution may be made up of water. Water may be present in the coagulant solution in an amount ranging from 70 wt % to 92 wt %, such as from 75 wt % to 90 wt %, such as from 80 wt % to 88 wt %.

Glove Formation

Figure 4:
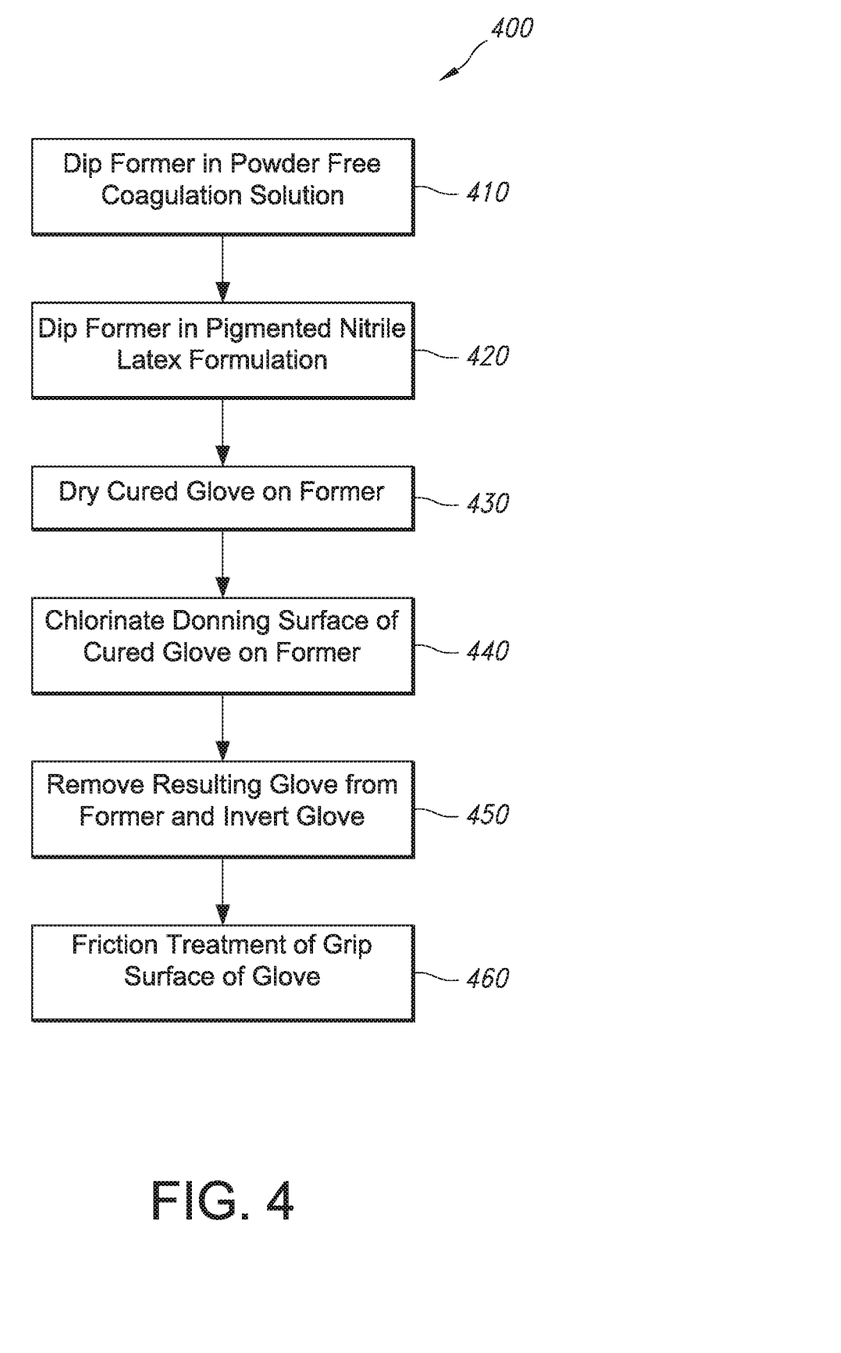
FIG. 4 illustrates a method of forming the elastomeric glove of the present invention.

The steps of a method 400 of formation of an elastomeric article of the present invention, in which the article is a glove, are shown generally in the flow chart of FIG. 4. The process 400 for forming an elastomeric glove entails providing a clean hand-shaped mold, also known as a "former". The former may be made from any suitable material that can be heated to a temperature of at least 130° C., such as ceramics and synthetic materials. For example, in one embodiment the former may be made of porcelain. The surface of the former defines the exterior or grip surface of the completed glove.

The former is conveyed on a central chain or conveyer belt through a preheated oven to evaporate any water present. The former may be preheated to a temperature ranging from approximately 55° C. to 60° C., for example about 58° C. At step 410, the former is then dipped into an aqueous coagulant solution prepared in accordance with the above description of the coagulant solution. The dip time for the solution can range from less than about 2 seconds to up to about 60 seconds. In one particular embodiment, a dip time between about 3 seconds and 10 seconds is desirable. For instance, the dip time can be about 5 seconds. The residual heat in the preheated former from the oven evaporates the water in the coagulant solution and leaves the former relatively uniformly coated with the residuals (i.e. at least the coagulant ions and the release agent).

In step 420, the coated former is then dipped into a bath of pigmented compounded nitrile rubber. The composition of the bath of pigmented compounded nitrile rubber is prepared in accordance with the above description of the nitrile rubber formulation. In one embodiment, the color pigment of the nitrile rubber formulation may be pink such that the compounded nitrile rubber is a pink pigmented compounded nitrile rubber.

During the dipping process, the coagulating agent, for example calcium ions, on the former causes the nitrile rubber to coalesce into a relatively uniform layer about the former, thus covering the coagulant formulation. The former is then withdrawn from the bath and the coagulated layer of nitrile rubber is permitted to fully coalesce. During the dipping process, the glove former is dipped in the nitrile rubber emulsion for a dwell time duration ranging from about 5 seconds up to about 60 seconds. Desirably, in a single-dip process, the dwell time of the dip may be between about 7 seconds and 12 seconds. In one embodiment, the dwell time may be between about 7 to 10 seconds. Only one dip may be necessary to attain the desired glove thickness in the palm area. However, multiple dips are possible, for example to thicken the nitrile rubber layer. In the case of a multiple-dip process, the dwell time of each of the dips may each be shorter than the dwell time of a single dip process.

During the aforementioned dip processes, faster entry and exit speeds of the glove former into the nitrile rubber formulation dipping solution can provide a more even thickness profile to the glove, due at least in part to the reduced difference in residence time of the fingertip and cuff areas of the formers in the compounded formulations. The former can be extracted from the dip bath at or near an initial vertical position and raised such that the finger tips are elevated to a horizontal or greater than horizontal position (e.g., tilted to an angle of about 20° to 45° above horizontal) for a brief period of time ranging from a few seconds to about 40 seconds. Quickly thereafter, the finger tips can be lowered to a position or angle between horizontal and initial vertical, while rolling the former along its longitudinal axis. The raising and lowering action can be repeated in a sinusoidal or wave-like motion. This process can enable the elastomeric material formulations (e.g., the nitrile rubber formulations) to distribute more evenly over the mold or former and produce a substrate product that is thinner overall.

After the step of dipping and removing the former from the nitrile rubber bath and the coalescence of the nitrile rubber layer, the former with the pigmented nitrile gel is then dipped into a leaching tank. In the leaching tank, hot water is circulated to remove water-soluble components, such as residual coagulant metallic salts (e.g. calcium nitrates) and other leachable material. The leaching process may take about 3 minutes to about 10 minutes at a water temperature ranging from about 49° C. to about 66° C. (about 120-150° F.).

At step 430, the former with pigmented nitrile rubber is then conveyed into an oven so that the pigmented nitrile gel is dried and cured at a temperature of about 100° C. to about 110° C. to evaporate any excess moisture from the surface of the formed glove.

The glove is then subjected to processing. During processing of the nitrile rubber glove according to the present invention, while the glove remains on the glove former, one side of the glove is subjected to halogenations (i.e., chlorination) in step 440. That is, the glove will have a chlorinated first surface forming a donning side of the glove once removed from the former. The former and glove are dipped in a sodium hypochlorite solution having a concentration ranging from about 1.5 wt % to about 4.5 wt %, such as from about 1.75 wt % to about 4.25 wt %, such as from about 2 wt % to about 4 wt %. The former and glove are then transferred from the sodium hypochlorite solution to a tank containing hydrochloric acid having a concentration ranging from about 0.1 wt % to about 1.5 wt %, such as from about 0.15 wt % to about 1.25 wt %, such as from about 0.2 wt % to about 1 wt %. In the tank of hydrochloric acid, a reaction takes place to generate hypochlorous acid on the surface of the glove. This process reduces the tackiness of the surface of the glove and causes the surface of the formed glove to become more slick. The next step is to rinse off excess chemicals from the chlorination process by dipping the former with the chlorinated glove into a series of 3 to 4 tanks of heated water. Each of the tanks of heated water may have a temperature ranging from about 85° C. to about 95° C., such as from about 87.5° C. to about 92.5° C., such as from about 89° C. to about 91° C. After the step of rinsing, the former with the chlorinated glove is transferred into a tunnel of ovens having a temperature ranging from about 70° C. to about 150° C., such as from about 80° C. to about 140° C., such as from about 90° C. to about 130° C., for another step of drying and curing the chlorinated glove. The drying and curing step of the chlorinated glove may last for about 30 minutes.

Next, the former with the cured, chlorinated glove is transferred to a stripping station. At the stripping station, in step 450, the glove is removed from the former and inverted to turn the glove inside out. By inverting the glove, the chlorinated surface of the glove becomes the inside of the glove and functions as an exemplary donning layer 110.

Upon formation and stripping of a plurality of gloves, the gloves are subjected to the final processing treatment, which may be termed the "friction treatment" to reduce friction on the grip surface of the gloves. The friction treatment is shown in FIG. 4 as step 460 of the process of formation of the glove and depicted in more detail in FIG. 5.

Figure 5:
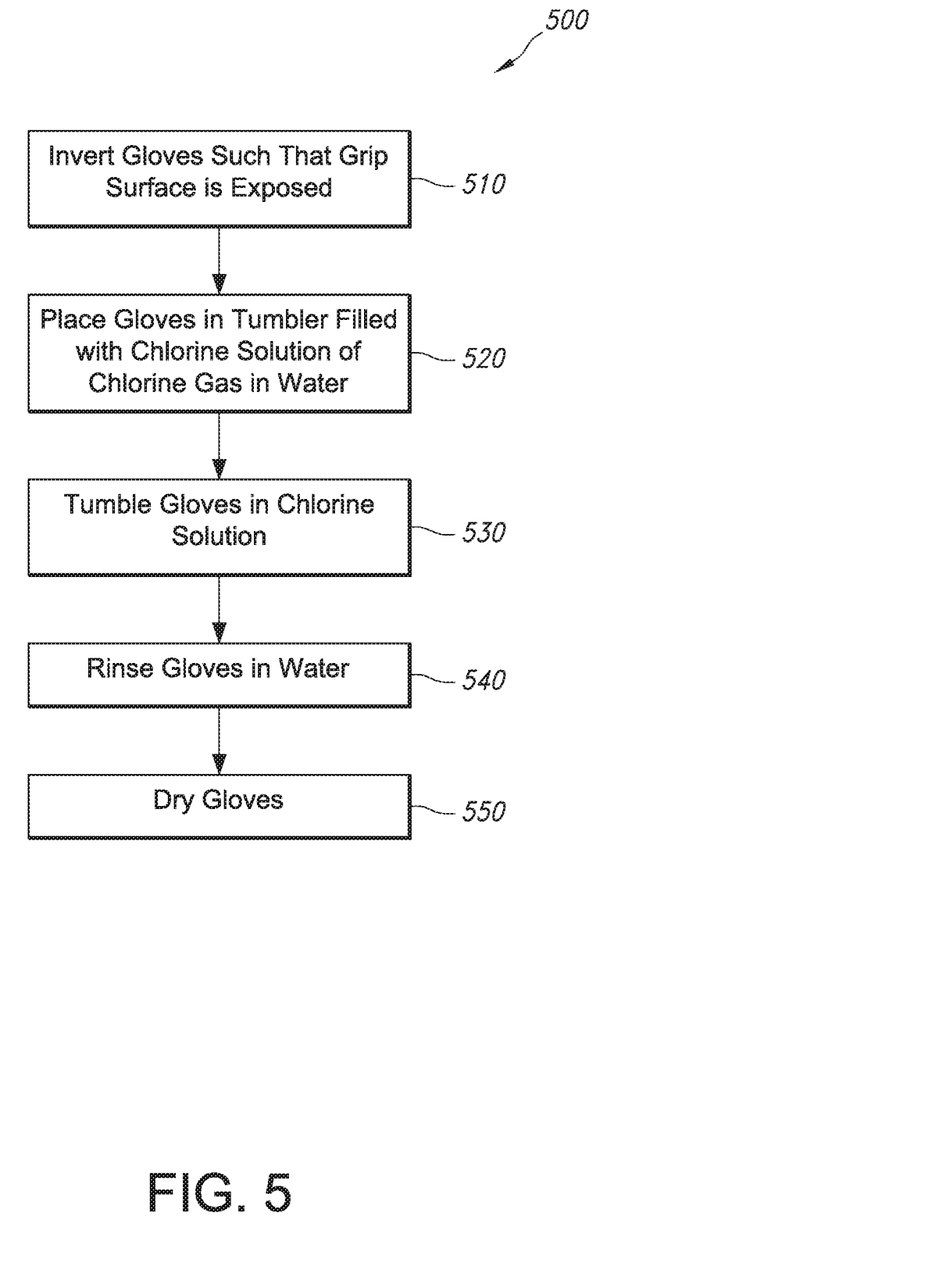
FIG. 5 illustrates a method of performing a friction treatment on a grip side of an elastomeric glove.

FIG. 5 shows the steps of the friction treatment 500. If not already performed, at step 510 the gloves stripped from the formers are inverted such that the grip surface 120 of each glove is exposed and the chlorinated donning surface 110 is inside the glove. Then, at step 520, a plurality of gloves, for example about 10,000 gloves, are transferred to a large tank, for example 1,000 gallons, where an additional chlorination step takes place to chlorinate the outside grip surface of the gloves. This step may be referred to as "off line chlorination" because it occurs after the formed gloves have been removed from the assembly line of formers. The large tank contains a chlorine solution. The chlorine solution may contain about 600-2200 parts per million (ppm) of chlorine gas dissolved in water, such as from about 700-1700 ppm, such as from about 800-1200 ppm. At step 530, the gloves are tumbled in the chlorine solution in the large tank for a duration of about 5 minutes to about 20 minutes, for example about 10 minutes. The chlorine solution may then be drained to waste. The large tank or tumbler may then be filled with water to rinse the chlorinated gloves of any residual chlorine left on the surface in step 540. The rinsing of step 540 can remove all residual chlorine from the grip surface of the gloves such that the grip surface is free of chlorine. Finally, after rinsing the gloves, the gloves may be transferred to a tumble dryer to remove any remaining moisture and provide a final drying process in step 550.

In one embodiment, the friction treatment chlorination may be performed as double chlorination. In a double chlorination treatment, after the initial chlorine solution is drained to waste after step 520, the large tank or tumbler then may be filled with another chlorine solution for a second chlorination of the grip surface of the gloves. The second chlorine solution may contain about 600-2200 parts per million (ppm) of chlorine gas dissolved in water, such as from about 700-1700 ppm, such as from about 800-1200 ppm. The gloves are tumbled in the second chlorine solution in the large tank for a duration of about 5 minutes to about 20 minutes, for example about 10 minutes. The second chlorine solution may then be drained to waste, and then steps 540 and 550 may be performed as described above to complete the friction treatment.

Following the final drying process of the gloves, the gloves may be packed into dispensers according to a required or desired quantity per dispenser. For example, 100 gloves may be packed into a dispenser or box.

Example 1

In Example 1, elastomeric gloves were made using a nitrile rubber formulation using the process described above, including chlorination of the donning surface of the gloves and off line chlorination of the grip surface of the gloves, and then subjected to mechanical testing. The nitrile rubber formulation included violet pigment and titanium dioxide to make pink pigmented gloves. After formation of the gloves and stripping of the gloves from the formers, the off line chlorination was performed on the grip side of the gloves by double chlorination at 800-1,200 ppm. Mechanical properties of the gloves were tested both before and after aging at 70° C.+/−2° C. for 168 hours+/−2 hours. The tensile testing parameters and methods are defined in American Society for Testing and Materials (ASTM) test standard D-412-98a. In the present invention, the ASTM protocol was employed with no changes. The testing apparatus used was an Intron® tonometer, model 5564, with a static load cell of capacity about +/−100N, and a XL extensometer. However, it is to be understood that other similar kinds of equipment could be used, as long as the machine met the requirements of the ASTM standard.

The gloves of Example 1 had an average cuff thickness of about 0.079 mm, an average palm thickness of about 0.09 mm, an average finger thickness of about 0.12 mm, and a glove length of about 310 mm. Further, the gloves of Example 1, before aging, had an average tensile strength of 39.09 MPa, an average force at break of about 10.11 N, and an average elongation at break of about 618.08%. After aging, the gloves of Example 1 had an average tensile strength of about 39.09 MPa, an average force at break of about 10.12 N, and an average elongation at break of about 581.10%. Further, the gloves of Example 1 are fully compliant with USP <800> to ensure effective protection by double gloving when handling, administering, compounding, or cleaning chemotherapy or other hazardous drugs. The gloves of Example 1 were tested in accordance with ASTM D6978 with 12 different chemotherapy drugs to be approved for use with chemotherapy drugs. The gloves of Example 1 additionally provided breach detection when wearing contrasting colored gloves as the outer layer for double gloving, for example a purple colored outer elastomeric glove. Moreover, the gloves of Example 1 meet or exceed the standards of ASTM D5151 and ASTM D6319.

Example 2

In Example 2, samples of a glove of the present invention and two different nitrile rubber gloves were tested to measure coefficient of friction on the grip surface of each of the gloves as explained in more detail below. As used herein, the "coefficient of friction" generally refers to relationship between the force of friction between two objects and the normal reaction between the objects that are involved. The coefficient of friction was tested by preparing testing specimens by mounting a 2 square inch section of the elastomeric material of each glove on a sled. Each specimen was pulled at 6 inches per minute across a stainless steel substrate. Each specimen was loaded with a 200-gram weight. Both the static coefficient of friction and the dynamic coefficient of friction were measured.

The three different nitrile gloves tested for coefficient of friction are as follows:

(1) A nitrile glove according to the present invention prepared in accordance with Example 1, referred to as the "Pink Under Guard," which had an average cuff thickness of about 0.079 mm, an average palm thickness of about 0.09 mm, an average finger thickness of about 0.12 mm. This glove has a chlorinated grip surface as described by the friction treatment above.

(2) A Halyard® STERLING® nitrile medical exam glove (a nitrile-butadiene rubber glove) which had an average palm thickness of about 0.08 mm. This glove has an unchlorinated grip surface.

(3) A Halyard® PURPLE® nitrile medical exam glove (a nitrile-butadiene rubber glove) which had an average cuff thickness of about 0.09 mm, an average palm thickness of about 0.12 mm, an average finger thickness of about 0.15 mm. This glove also has an unchlorinated grip surface.

The individual test results, along with the average and standard deviation for three sub-samples of each glove type are provided in Tables 1 and 2 below.

TABLE 1

Static Coefficient of Friction
Static Coefficient, µ

| Sample | Product | | |
| --- | --- | --- | --- |
| Number | Sterling Nitrile | Purple Nitrile | Pink Under Guard |
| 1 | >2.65* | 2.22 | 0.559 |
| 2 | >2.75* | 2.20 | 0.638 |
| 3 | >2.63* | 2.32 | 0.659 |
| Avg | >2.68* | 2.24 | 0.619 |
| Std Dev | 0.063 | 0.063 | 0.052 |

*Specimens too tacky to obtain reading

TABLE 2

Dynamic Coefficient of Friction
Dynamic Coefficient, µ

| Sample | Product | | |
| --- | --- | --- | --- |
| Number | Sterling Nitrile | Purple Nitrile | Pink Under Guard |
| 1 | * | 1.83 | 0.574 |
| 2 | * | 1.79 | 0.639 |
| 3 | * | 2.01 | 0.726 |
| Avg | * | 1.88 | 0.646 |
| Std Dev | | 0.120 | 0.076 |

*Specimens too tacky to obtain reading

As shown in Tables 1 and 2, the specimens of the comparative STERLING® glove were too tacky to obtain readings for the dynamic coefficient of friction. As shown in Table 1, both the comparative STERLING® glove and the comparative PURPLE® glove have an average static coefficient of friction of over 2.20, whereas the gloves of the present invention ("Pink Under Guard") having a friction-treated grip surface exhibit an average coefficient of friction of about 0.619. As shown in Table 2, the comparative PURPLE® glove has an average dynamic coefficient of friction of 1.88, whereas the gloves of the present invention ("Pink Under Guard") having a friction-treated grip surface exhibit an average dynamic coefficient of friction of about 0.646.

The present invention has been described both in general and in detail by way of examples. These and other modifications and variations of the present invention may be practiced by those of ordinary skill in the art, without departing from the spirit and scope of the present invention. In addition, it should be understood that aspects of the various embodiments may be interchanged both in whole and in part. Furthermore, those of ordinary skill in the art will appreciate that the foregoing description is by way of example only and is not intended to limit the invention so further described in such appended claims.

What is claimed is:

1. An elastomeric article comprising:
   an article comprising a flexible layer of elastomeric nitrile rubber formed from a nitrile rubber emulsion, the article having a first surface and a second surface;
   wherein the first surface and the second surface are chlorinated, wherein chlorination of the first surface and chlorination of the second surface are accomplished with different chlorine solutions, wherein chlorination of the first surface is accomplished by dipping the first surface into a sodium hypochlorite solution followed by dipping the first surface into a tank of hydrochloric acid;

wherein the second surface is treated with a friction treatment that reduces the level of friction of the second surface to improve the ease with which a second elastomeric article can slide on top of the second surface, wherein the friction treatment of the second surface comprises the chlorination of the second surface, wherein the second surface has a static coefficient of friction in a range from about 0.3 to about 0.9 or a dynamic coefficient of friction in a range from about 0.3 to about 1.

2. The elastomeric article of claim 1, wherein the article is a glove.

3. The elastomeric article of claim 2, wherein the first surface is a donning side of the glove and the second surface is a grip side of the glove.

4. The elastomeric article of claim 1, wherein the second surface is chlorinated with a solution of chlorine gas in water.

5. The elastomeric article of claim 1, wherein the nitrile rubber emulsion includes a solids content of between about 15 percent and about 30 percent, by weight.

6. The elastomeric article of claim 1, wherein the nitrile rubber emulsion includes a defoamer.

7. The elastomeric article of claim 1, wherein coagulation of the nitrile rubber emulsion to form the elastomeric article is accelerated by a metallic salt, wherein the metallic salt includes nitrate, sulfate, or chloride salts of calcium, aluminum, or zinc, or a combination thereof.

8. The elastomeric article of claim 1, wherein the friction treated second surface has less friction compared to an identically formed elastomeric article that has not been treated with the friction treatment.

9. A process for making an elastomeric article, the process comprising steps of:
coating a surface of a former with a coagulant solution;
immersing the former into a nitrile rubber emulsion to form a layer of coagulated nitrile rubber on the former surface, the coagulated nitrile rubber forming an elastomeric article on the former, the elastomeric article having a first surface that is exposed from the former and a second surface contacting the former;
chlorinating the first surface of the elastomeric article, wherein chlorinating the first surface comprises dipping the former containing the elastomeric article into a first solution of sodium hypochlorite, then transferring the former containing the elastomeric article to a tank containing a second solution of hydrochloric acid;
curing the elastomeric article;
removing the elastomeric article from the former and inverting the elastomeric article such that the chlorinated first surface of the elastomeric article becomes an interior surface of the elastomeric article; and
subjecting the inverted elastomeric article to a friction treatment to reduce the friction of the second surface of the elastomeric article, wherein the second surface has a static coefficient of friction in a range from about 0.3 to about 0.9 or a dynamic coefficient of friction in a range from about 0.3 to about 1 wherein the friction treatment of the second surface comprises chlorination of the second surface.

10. The process of claim 9, wherein the elastomeric article is a glove, further wherein the first surface forms a donning surface of the glove and the second surface forms a grip surface of the glove.

11. The process of claim 9, wherein the nitrile rubber emulsion includes a solids content of between about 15 percent and about 30 percent, by weight.

12. The process of claim 9, wherein the nitrile rubber emulsion is pigmented such that the elastomeric article is colored by the pigment.

13. The process of claim 9, wherein the step of immersing the former into the nitrile rubber emulsion lasts for a dwell time sufficient to form a layer of coagulated nitrile rubber on the former surface having a thickness in the range of about 0.06 mm to about 0.14 mm.

14. The process of claim 9, wherein the first solution comprises from about 1.5 wt % to about 4.5 wt % sodium hypochlorite, and the second solution comprises from about 0.1 wt % to about 1.5 wt % hydrochloric acid.

15. The process of claim 14, wherein the former containing the elastomeric article is dipped into a series of water tanks at about 85° C. to about 95° C. after the step of transferring the former containing the elastomeric article to the tank containing the second solution.

16. The process of claim 9, wherein the friction treatment comprises immersing the inverted elastomeric article into a chlorinating bath to chlorinate the former surface of the elastomeric article.

17. The process of claim 16, wherein the step of immersing the inverted elastomeric article into the chlorinating bath comprises transferring the inverted elastomeric article to a tank containing a chlorine solution containing about 600 ppm to about 2200 ppm of chlorine gas dissolved in water and tumbling the elastomeric article in the solution within the tank.

18. The process of claim 17, further comprising draining the chlorine solution to waste and filling the tank with water to clean the chlorinated elastomeric article of any residual chlorine left on the second surface of the elastomeric article.

19. A kit for double-gloving, the kit comprising:
a first elastomeric glove formed from a flexible layer of elastomeric nitrile rubber formed from a nitrile rubber emulsion, the glove having a chlorinated first surface and a friction treated second surface, wherein the chlorination of the first surface and the friction treatment of the second surface are accomplished with different chlorine solutions, wherein chlorination of the first surface is accomplished by dipping the first surface into a sodium hypochlorite solution followed by dipping the first surface into a tank of hydrochloric acid; and
a second elastomeric glove for donning on top of the first elastomeric glove;
wherein the friction treatment of the second surface of the first elastomeric glove reduces the level of friction of the second surface to improve the ease with which the second elastomeric glove can slide on top of the second surface to don the second elastomeric glove on top of the first elastomeric glove, wherein the second surface has a static coefficient of friction in a range from about 03 to about 0.9 or a dynamic coefficient of friction in a range from about 0.3 to about 1 wherein the friction treatment of the second surface comprises chlorination of the second surface.

* * * * *